(12) United States Patent
Jansson et al.

(10) Patent No.: US 7,888,549 B2
(45) Date of Patent: Feb. 15, 2011

(54) ABSORBENT ARTICLE

(75) Inventors: Filip Jansson, Göteborg (SE); Marie Johansson, Mölnlycke (SE); Fredrik Asp, Onsala (SE)

(73) Assignee: SCA Hygiene Products AB, Gothenburg (SE)

( * ) Notice: Subject to any disclaimer, the term of this patent is extended or adjusted under 35 U.S.C. 154(b) by 0 days.

(21) Appl. No.: 11/806,037

(22) Filed: May 29, 2007

(65) Prior Publication Data

US 2007/0233029 A1    Oct. 4, 2007

Related U.S. Application Data

(63) Continuation of application No. PCT/SE2004/001759, filed on Nov. 30, 2004.

(51) Int. Cl.
*A61F 13/20* (2006.01)
*A61F 13/15* (2006.01)

(52) U.S. Cl. .............................. 604/380; 604/385.101; 604/385.201

(58) Field of Classification Search ......... 604/317–326, 604/378–384, 385.01–385.14
See application file for complete search history.

(56) References Cited

U.S. PATENT DOCUMENTS

| | | | | |
|---|---|---|---|---|
| 4,631,062 A * | 12/1986 | Lassen et al. | ........... | 604/385.02 |
| 5,895,380 A | 4/1999 | Turi et al. | | |
| 6,440,115 B1 | 8/2002 | Connelly et al. | | |
| 6,563,013 B1 * | 5/2003 | Murota | ........................ | 604/380 |
| 6,689,935 B2 * | 2/2004 | Chen et al. | .................. | 604/378 |
| 7,005,558 B1 * | 2/2006 | Johansson et al. | ........... | 604/383 |
| 7,078,583 B2 * | 7/2006 | Kudo et al. | .................. | 604/380 |
| 7,207,978 B2 | 4/2007 | Takino et al. | | |
| 2002/0123732 A1 * | 9/2002 | Koyama et al. | ........ | 604/385.24 |

FOREIGN PATENT DOCUMENTS

| | | | |
|---|---|---|---|
| EP | 0 734 240 | B1 | 10/1996 |
| EP | 0 758 543 | B1 | 2/1997 |
| EP | 0 769 284 | A1 | 4/1997 |
| EP | 0 969 784 | B1 | 1/2000 |
| EP | 1 008 333 | A2 | 6/2000 |
| EP | 1 035 818 | B1 | 9/2000 |
| EP | 1 210 926 | A2 | 6/2002 |
| EP | 1 384 459 | B1 | 1/2004 |
| EP | 1 495 739 | A1 | 1/2005 |

(Continued)

OTHER PUBLICATIONS

International Search Report dated Jul. 6, 2005.

(Continued)

*Primary Examiner*—Leslie R Deak
*Assistant Examiner*—Philip R Wiest
(74) *Attorney, Agent, or Firm*—Buchanan Ingersoll & Rooney PC (57) ABSTRACT

An absorbent article having an absorbent core and a cover enclosing the absorbent core. The absorbent core is provided with at least two slits or grooves diverging from a crotch region of the absorbent core in a direction towards one transverse edge of the absorbent core and terminating inside the respective longitudinal edge as well as the respective transverse edge of the absorbent core. These slits or grooves form folding guides along which the article can be formed into a shape having a narrow crotch width.

24 Claims, 5 Drawing Sheets

FOREIGN PATENT DOCUMENTS

| | | | |
|---|---|---|---|
| GB | 2 319 730 A | 6/1998 |
| JP | 09-173381 A | 7/1997 |
| JP | 2001-340383 A | 12/2001 |
| JP | 2003-275241 A | 9/2003 |
| RU | 2002 111 570 A | 12/2003 |
| WO | 95/00763 A1 | 1/1995 |
| WO | WO 01/24754 A1 | 4/2001 |
| WO | 2005/122984 A1 | 12/2005 |

OTHER PUBLICATIONS

Written Opinion of the International Searching Authority dated Jul. 6, 2005.

Translation of Official Action issued in corresponding Russian application.

Notice of Reasons for Rejection issued on Mar. 2, 2010 in corresponding Japanese Patent Application No. 2007-542964.

* cited by examiner

ABSORBENT ARTICLE

TECHNICAL FIELD

The present invention refers to an absorbent article, such as a diaper, pant diaper, incontinent brief, sanitary napkin and the like intended to absorb and retain body fluid of the wearer.

BACKGROUND

Absorbent articles of the above mentioned kind are known in which slits are created, said slits extending through the entire or part of the thickness of an absorbent core in order to promote the spread of body liquid along said slits. Such longitudinally extending distribution slits are known from EP-A-0 758 543. The slits extend in the longitudinal direction of the absorbent core and are located in parallel. The inner and outer cover of the absorbent core, in the form of a topsheet and a backsheet, are bonded to each other along the slits to form linear grooves extending along the slits.

An absorbent core in a diaper is further known from EP-A-0 734 240, which comprises a main body having a leg recess at each side thereof and two side bodies placed laterally outside the main body on respective sides thereof and in the respective leg recess. There is a gap between the main body and the side bodies and the outer and inner cover sheets are joined to each other in the gaps between the main body and the side bodies. Contraction of the leg elastics of the diaper will cause the side bodies to swing upwards and thus create a basin shape formed by the main body and the upraised side bodies.

It is further known from various prior art documents to provide compressed grooves in an absorbent core in order to promote distribution of body fluids along said grooves. Examples of documents disclosing such compressed grooves are WO 95/0763 and U.S. Pat. No. 6,563,013.

Absorbent articles having an improved comfort by narrowing the width of the area where the article is applied in the crotch of the wearer (crotch area) during use are known through a number of prior art documents, for example EP-A-1 384 459, which discloses a minimum width of the article in the crotch area of from 250 to 350 mm. However if the width of the crotch portion is too narrow, the absorption capacity in this area, where the body fluid is discharged, will be insufficient and leakage is likely to occur.

OBJECTS AND SUMMARY

One object of the present invention is to provide an absorbent article which has an improved comfort and which can easily be shaped from a broader into a more narrow width in the crotch region, while at the same time maintaining a sufficient absorption capacity in this region.

Another object is to provide an absorbent article having an absorbent core which may easily be shaped into a basin-shape for improved liquid collecting capacity and reduced leakage risk.

These and further objects have according to the invention been achieved by an absorbent article comprising an absorbent core and a cover enclosing the absorbent core, said cover comprising a liquid pervious inner cover on the wearer facing side of the absorbent core and a liquid impervious outer cover on the garment facing side of the absorbent core, said article having a longitudinal and a transverse direction and comprises as seen in its longitudinal direction a front portion, a back portion and a crotch portion there between, said absorbent core having an elongated shape and comprising a pair of longitudinal edges and a front and a back transverse edge, said core having a crotch region and at least one outer region as seen in the longitudinal direction of the article, said outer region(-s) being located adjacent the respective transverse edge of the core, said absorbent core further being provided with at least two slits or grooves, which are arranged to diverge from the crotch region of the absorbent core in a direction towards one transverse edge thereof and terminate inside the respective longitudinal edge as well as the respective transverse edge of the absorbent core.

These diverging slits or grooves act as folding guides along which the absorbent core can be folded to narrow the crotch width of the article and create a basin shape which is efficient in collecting and holding discharged body fluid. They also contribute in giving the product a more anatomic shape.

According to one embodiment said at least two slits or grooves are separated and not directly communicating with each other at their converging ends in the crotch region of the absorbent core.

According to an alternative embodiment said at least two slits or grooves are communicating with each other at their converging ends in the crotch region of the absorbent core so as to form a V-shape.

According to one aspect of the invention said at least two slits or grooves are areas having a lower basis weight than the surrounding areas of the absorbent core. In a further aspect the slits or grooves are cuts. It is preferred that said at least two slits or grooves extend through at least half the thickness of the absorbent core.

In a further embodiment said at least two slits or grooves extend through the entire thickness of the absorbent core.

According to a further aspect of the invention the at least two diverging slits or grooves form an angle of from 5° to 135°, preferably from 10° to 120° and more preferably from 20° to 60° to each other.

In one aspect of the invention the slits or grooves have length of at least 20 mm, preferably at least 30 mm. In a further aspect they have a width of from 1 to 25 mm, preferably from 3 to 20 mm and more preferably from 5 to 15 mm.

It is preferred that that said at least two slits or grooves are arranged to diverge in a direction towards the front transverse edge of the absorbent core.

According to one embodiment at least four slits or grooves are provided, at least two of which are diverging in a direction towards the front transverse edge and at least two are diverging in a direction towards the back transverse edge of the absorbent core. It is preferred that the at least two slits or grooves diverging towards the front transverse edge and the at least two slits or grooves diverging towards the back transverse end are arranged on opposite sides of a transverse crotch line extending through a crotch point as defined in the specification.

In one aspect of the invention the at least two slits or grooves diverging towards the front transverse edge are spaced apart from the at least two slits or grooves diverging towards the back transverse end a smallest distance b in longitudinal direction y of at least 5 mm, preferably at least 10 mm and more preferably at least 20 mm.

According to a further aspect of the invention one or more notches are provided at the respective longitudinal edges of the absorbent core in the crotch region thereof.

In one embodiment the absorbent core has a substantially rectangular shape.

DESCRIPTION OF DRAWINGS

The embodiments of the invention will in the following be closer described with reference to some embodiments shown in the accompanying drawings.

DEFINITIONS

Absorbent Article

The term "absorbent article" refers to products that are placed against the skin of the wearer to absorb and contain body exudates, like urine, faeces and menstrual fluid. The invention mainly refers to disposable absorbent articles, which are articles that are not intended to be laundered or otherwise restored or reused as an absorbent article after use.

Inner Liquid Permeable Cover

The inner liquid permeable cover forms the inner cover of the absorbent article and in use is placed in direct contact with the skin of the wearer. The inner liquid permeable cover can comprise a nonwoven material, e.g., spunbond, meltblown, carded, hydroentangled, wetlaid etc. Suitable nonwoven materials can be comprised of natural fibers, such as woodpulp or cotton fibers, manmade fibers, such as polyester, polyethylene, polypropylene, viscose etc. or from a mixture of natural and manmade fibers.

The inner liquid permeable cover material may further be composed of tow fibers, which may be bonded to each other in a bonding pattern, as e.g., disclosed in EP-A-1 035 818.Further examples of inner liquid permeable cover materials are porous foams, apertured plastic films etc. The materials suited as inner liquid permeable cover materials should be soft and non-irritating to the skin and be readily penetrated by body fluid, e.g., urine or menstrual fluid. The inner liquid permeable cover may further be different in different parts of the absorbent article.

Outer Liquid Impermeable Cover

The outer liquid impermeable cover forms the outer cover of the absorbent article at least on the core area thereof. The outer liquid impermeable cover can comprise a thin plastic film, e.g., a polyethylene or polypropylene film, a nonwoven material coated with a liquid impervious material, a hydrophobic nonwoven material, which resists liquid penetration, or a laminate, e.g., of a plastic film and a nonwoven material. The outer liquid impermeable cover material may be breathable so as to allow vapour to escape from the absorbent core, while still preventing liquids from passing through. Examples of breathable outer liquid impermeable cover materials are porous polymeric films, nonwoven laminates from spunbond and meltblown layers, laminates from porous polymeric films and nonwoven materials.

Absorbent Core

The "absorbent core" is the absorbent structure disposed between the two covers of the absorbent article. The absorbent core 5 can be of any conventional kind. Examples of commonly occurring absorbent materials are cellulosic fluff pulp, tissue layers, highly absorbent polymers (so called superabsorbents), absorbent foam materials, absorbent nonwoven materials or the like. It is common to combine cellulosic fluff pulp with superabsorbent polymers in an absorbent core. Superabsorbent polymers are water-swellable, water-insoluble organic or inorganic materials capable of absorbing at least about 20 times its weight and in an aqueous solution containing 0.9 weight percent of sodium chloride. Organic materials suitable for use as a superabsorbent material can include natural materials such as polysaccharides, polypeptides and the like, as well as synthetic materials such as synthetic hydrogel polymers. Such hydrogel polymers include, for example, alkali metal salts of polyacrylic acids, polyacrylamides, polyvinyl alcohol, polyacrylates, polyacrylamides, polyvinyl pyridines, and the like. Other suitable polymers include hydrolyzed acrylonitrile grafted starch, acrylic acid grafted starch, and isobutylene maleic anhydride copolymers and mixtures thereof. The hydrogel polymers are preferably lightly crosslinked to render the material substantially water insoluble. Preferred superabsorbent materials are further surface crosslinked so that the outer surface or shell of the superabsorbent particle, fiber, flake, sphere, etc. possesses a higher crosslink density than the inner portion of the superabsorbent. The superabsorbent materials may be in any form suitable for use in absorbent composites including particles, fibers, flakes, spheres, and the like.

A high absorption capacity is provided by the use of high amounts of superabsorbent material. For an absorbent core comprising a matrix of hydrophilic fibers, such as cellulosic fibers, and superabsorbent material, the proportion of superabsorbent material is preferably between 10 and 90% by weight, more preferably between 30 and 70% by weight.

It is conventional in absorbent articles to have absorbent cores comprising layers of different properties with respect to liquid receiving capacity, liquid distribution capacity and storage capacity. The thin absorbent bodies, which are common in for example baby diapers and incontinence guards, often comprise a compressed mixed or layered structure of cellulosic fluff pulp and superabsorbent polymers. The size and absorbent capacity of the absorbent core may be varied to be suited for different uses such as for infants or for adult incontinent persons.

The absorbent core may further include an acquisition distribution layer placed on top of the primary absorbent body and which is adapted to quickly receive and temporarily store discharged liquid before it is absorbed by the primary absorbent core. Such acquisition distribution layers are well known in the art and may be composed of porous fibrous waddings or foam materials.

Crotch Point and Crotch Line

Figure 6:
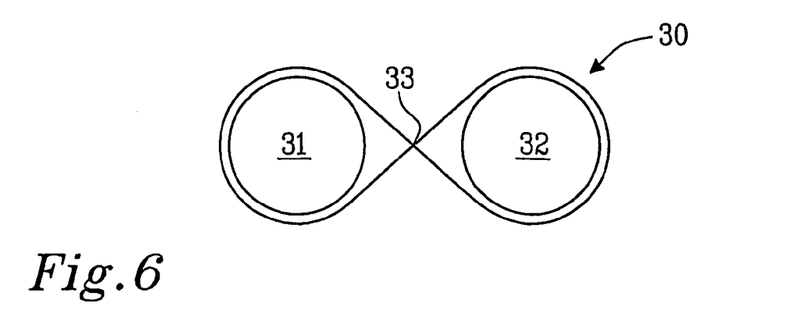
FIG. 6 illustrates how the crotch point of a wearer, an absorbent article and the corresponding absorbent core is determined.

The crotch point of an absorbent article and of the absorbent core of an absorbent article is defined in, for example, EP-B1-0 969 784,i.e., it is determined by placing the article on a wearer in a standing position and then placing an extensible filament 30 around the legs 31, 32 in a figure eight configuration (FIG. 6). The point in the article and the absorbent core corresponding to the point of intersection of the filament is deemed to be the crotch point 33. It is understood that the crotch point is determined by placing the absorbent article on the wearer in the intended manner and determining where the crossed filament would contact the article/core. The crotch line a is a line in the transverse direction, x, of the article/core extending through the crotch point 33.

Crotch Region

In a normal case the "crotch region" 12 is determined by first locating the crotch point 33 of the absorbent core, and then measuring forward and backward a distance of 25% of the total length of the core. In a case, in which the absorbent core is located asymmetrically in the article, for example the main part of the core is located towards the front of the article and the rear edge of the core is located a distance from the crotch point which is equal to or less than 25% of the total length of the core, the crotch region extends from the rear end of the core, to the crotch point 33 and a distance forwards which is 25% of the total length of the core, or vice versa in case the main part of the core is located towards the back of the article. Thus in the normal case the "crotch region" of the absorbent core corresponds to 50% of the total length of the absorbent core (i.e., in the longitudinal direction, y direction), where the crotch point 33 is located in the longitudinal center of the crotch region. For an asymmetrically placed core, as described above, the crotch region 12 may be shorter than 50% of the total length of the core and the crotch point 33 may be located outside the longitudinal center of the crotch region 12.

DESCRIPTION OF PREFERRED EMBODIMENTS

Figure 1:
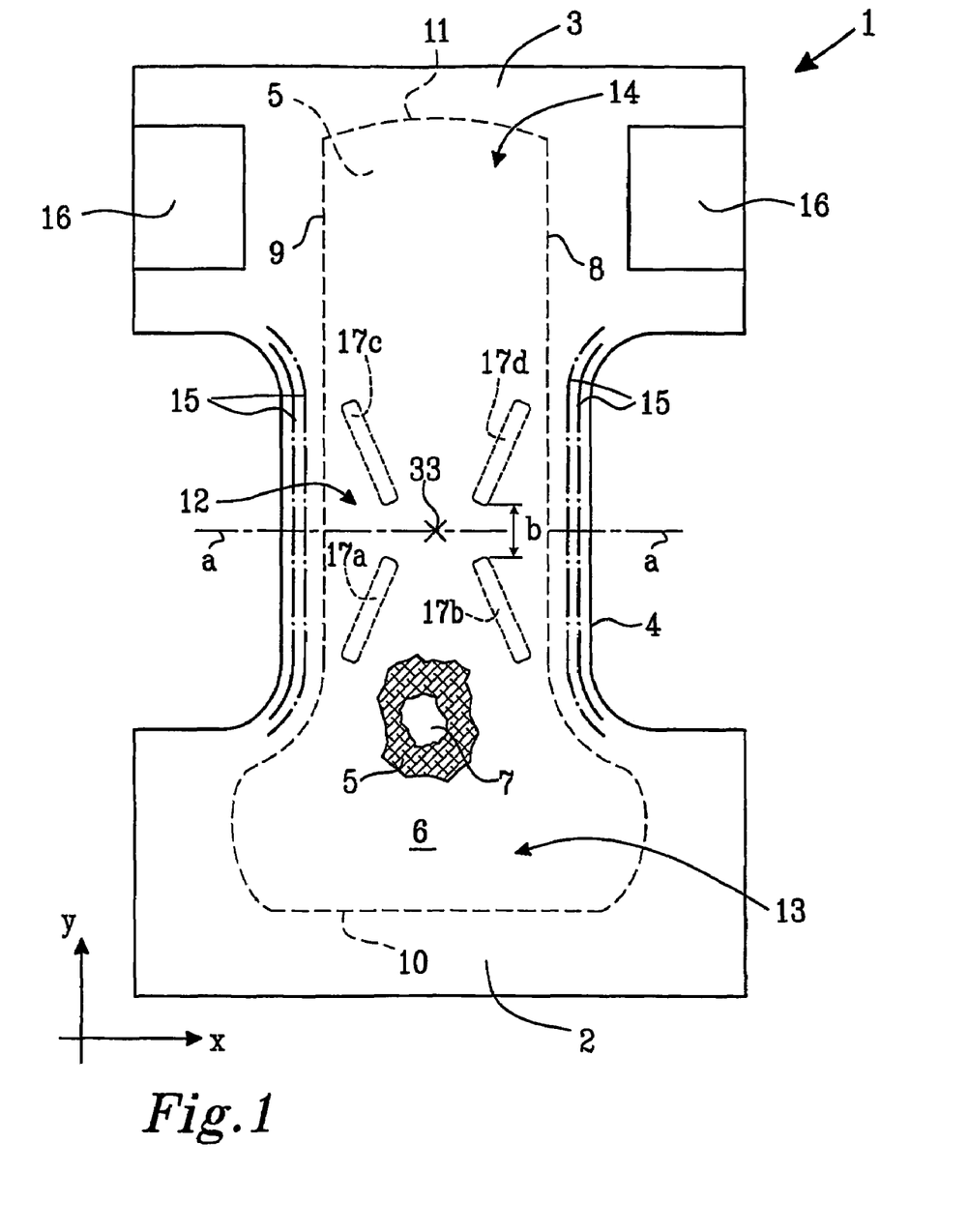
FIG. 1 shows a simplified plan view of an absorbent article in the form of a diaper in its flat, uncontracted state prior to formation.

FIG. 1 shows a simplified plan view of an absorbent article in a flat, uncontracted state. The term "absorbent article" refers to products that are placed against the skin of the wearer to absorb and contain body exudates, like urine, feces and menstrual fluid. The invention mainly refers to disposable absorbent articles, which means articles that are not intended to be laundered or otherwise restored or reused as an absorbent article after use.

The absorbent article shown in FIG. 1 is in the form of a diaper 1 having a longitudinal, y, and a transverse direction, x, and comprises, as seen in its longitudinal direction, a front portion 2, a back portion 3 and a crotch portion 4 there between. In its most common form the diaper comprises an absorbent core 5 and a cover enclosing the absorbent core. Said cover comprises an inner liquid pervious cover 6 on the wearer facing side of the absorbent core 5 and an outer liquid impervious cover 7 on the garment facing side of the absorbent core. The inner liquid pervious cover 6 is often referred to as topsheet, while the outer liquid impervious cover 7 is often referred to as backsheet.

The absorbent core 5 has an elongated shape and comprises a pair of longitudinal edges 8, 9 and a pair of transverse edges 10, 11. The absorbent core 5 has a crotch region 12 and two outer regions 13, 14 as seen in the longitudinal direction, y, of the article. The outer regions 13, 14 are located adjacent the respective transverse edges 10, 11 of the core. The crotch region 12 is the region of the core as defined above. For an article having a core 5 which is placed asymmetrically in the article, the core may have only one outer region 13 or 14 and a crotch region 12, wherein one of the transverse edges 10 or 11 may form the termination of the crotch region 12 in one longitudinal direction.

The inner cover 6 and the outer cover 7 extend outward beyond the peripheral edges of the absorbent core 5 and have their inner surfaces bonded to each other, e.g., by gluing or welding by heat or ultrasonic. The inner and outer cover materials may further be bonded, e.g., by adhesive, to the absorbent core.

The areas of the article adjacent the leg openings are along the longitudinal side edges provided with elastic members 15 which are bonded between the inner cover 6 and the outer cover 7 material layers in a stretched condition so as to provide elasticized leg openings of the diaper. Corresponding elastic members (not shown) may be arranged to extend in the transverse, x, direction in the front 2 and back portion 3 adjacent the transverse side edges forming the waist opening of the diaper.

The back portion 3 is provided with fasteners 16 attached thereto. The fasteners are intended to be fastened to the front region of the article to form a pant-like shape. The fasteners 16 may be in the form of adhesive tapes or hook elements adapted to attach to a loop material, for example, in the form of a nonwoven material forming the outer coversheet of the diaper.

The absorbent core 5 is formed with four slits or grooves 17a-d, two of which, 17 a and b, are extending from the crotch region 12 close to the crotch line a and are diverging in a direction towards the transverse edge 10 of the absorbent core 5, and two of which, 17 c and d, are extending from the crotch region 12 on the opposite side of the crotch line a and are diverging an a direction towards the opposite transverse edge 11 of the absorbent core 5. The slits or grooves 17a-d may be formed by areas having a lower basis weight than the surrounding areas of the absorbent core 5. Preferably they extend through at least half the thickness of the absorbent core. In one embodiment they extend through the entire thickness of the absorbent core. In a case where the absorbent core comprises two or more layers, the slits or grooves may extend through one, more or all layers.

The inner 6 and outer cover 7 materials may be joined to each other through the slits or grooves 17a-d in case these extend through the entire thickness of the absorbent core 5, but the inner and outer covers may alternatively be free from each other in the area of the slits or grooves 17a-d.

In another embodiment the slits or grooves 17a-d are cuts made through the entire or part of the thickness of the absorbent core 5.

In a still further embodiment the slits or grooves 17a-d are compressed grooves having a higher density than the surrounding regions of the absorbent core.

Two of the slits 17a, b are diverging in a direction towards the front outer region 13 and the front transverse edge 10 of the absorbent core 5, while two slits 17c, d are diverging in a direction towards the back outer region 14 and the back transverse edge 11 of the absorbent core 5. The slits or grooves 17a-d do not extend all the way to the respective longitudinal edge 8 and 9 nor to the respective transverse edge 10 and 11 of the absorbent core 5, but terminate inside said edges, preferably at least 5 mm and more preferably at least 10 mm inside thereof.

In a preferred embodiment the slits or groves 17a-d have an extension in the longitudinal direction, y, of the article that does not go beyond the crotch region 12 of the absorbent core 5.

The number of slits or grooves 17a-d may vary, but should at least be two, and which preferably are arranged in the front part of the crotch region 12 of the absorbent core 5.

The diverging slits or grooves 17a and b, and 17c and d respectively, form an angle of from 5° to 135°, preferably from 10° to 120°, more preferably from 20 to 60°, to each other.

In the embodiment shown in FIG. 1 the slits or grooves 17*a-d* are separated and are not communicating with each other at their converging ends in the crotch region 12 of the absorbent core. In an alternative embodiment, as shown in FIG. 5*b*,the slits or grooves 17*a* and *b* in the front region are connected at their converging ends, thus forming a V-shape. Also the slits 17*c* and *d* in the back portion may of course be connected to form a V-shape in a corresponding manner.

The slits or grooves 17*a-d* do preferably not extend all the way to the transverse crotch line a (FIG. 1) of the core. Thus there will be a space in the crotch region 12 adjacent said crotch line a and the crotch point 33, which is free from said slits or grooves 17*a-d*.The distance in longitudinal direction between the crotch line a and the respective end of the slits or grooves 17*a-d* facing the crotch line a is preferably 2.5 mm, more preferably at least 5 mm and most preferably at least 10 mm. This means that the smallest distance b in longitudinal direction between the opposed ends of the slits or grooves 17*a* and 17*c* and the opposed slits or grooves 17 *b* and *d* diverging towards the front and back portion respectively is preferably at least 5 mm, more preferably at least 10 mm and most preferably at least 20 mm.

The length and width of the grooves or slits may vary depending on the type and size of the absorbent article, for example whether the article is intended for babies or for incontinent adults. The length of the slits or grooves is, however, preferably at least 20 mm, and more preferably at least 30 mm. In a case where the slits or grooves are "broken", i.e., consist of a row of two or more short slits or grooves, the length is defined as the total length of the row of short slits or grooves.

The width of the slits or grooves is between 1 and 25 mm, preferably between 5 and 20 and more preferably between 3 and 15 mm.

Figure 2:
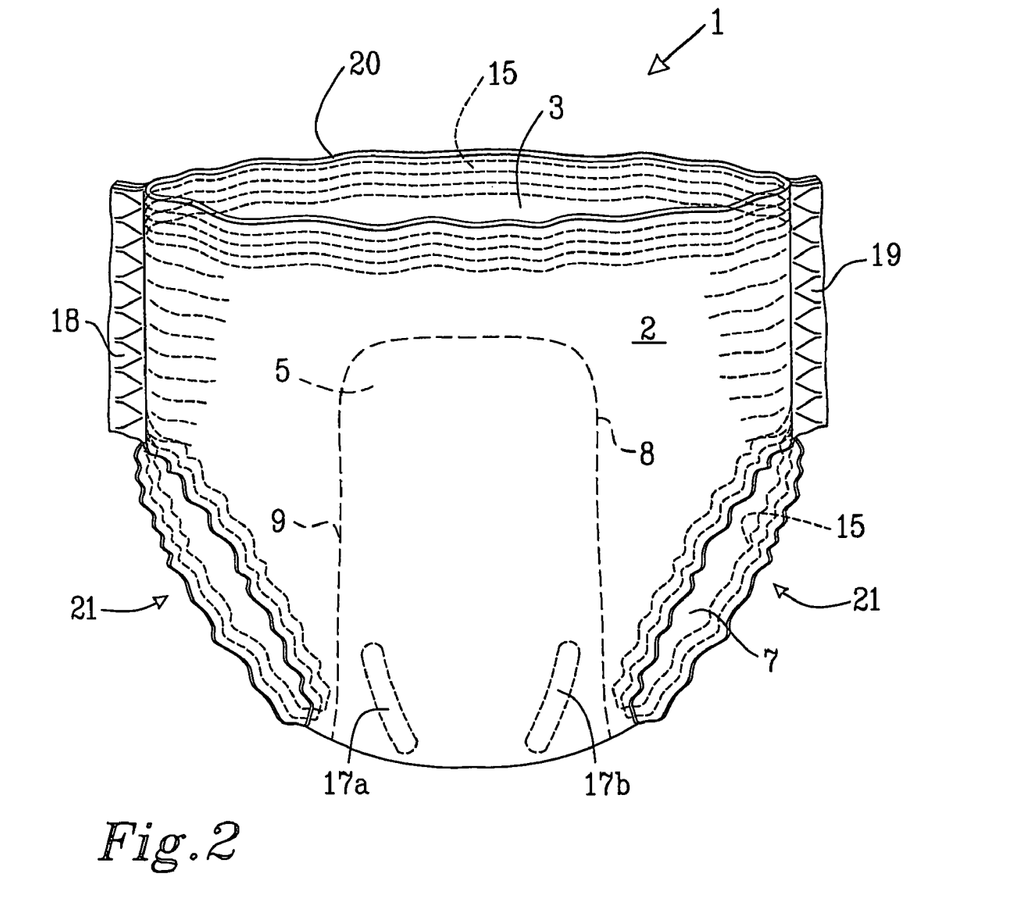
FIG. 2 shows a perspective view of a pant diaper.
Figure 3:
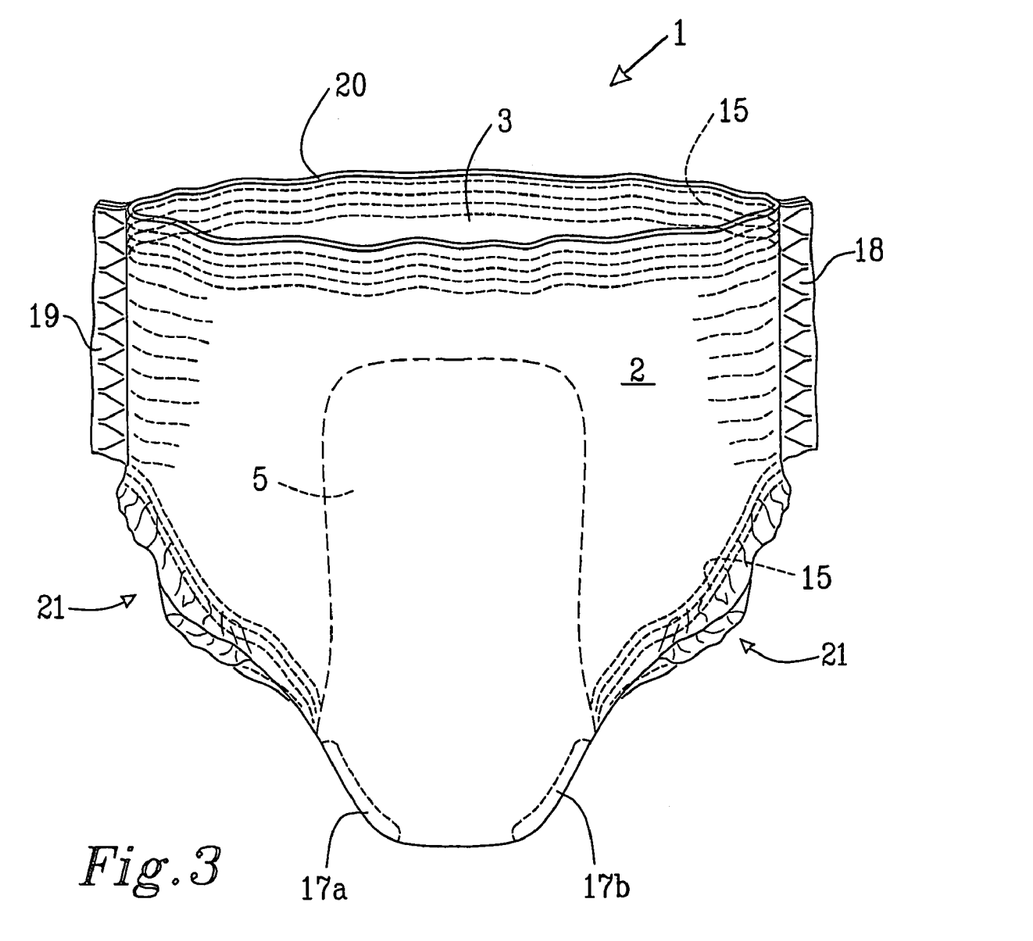
FIG. 3 shows a perspective view of the same pant diaper but in a state where it has been shaped to a narrow crotch width.

FIGS. 2 and 3 show a so called pant diaper in which the front and back portions 2 and 3 are joined to each other along their longitudinal side edges thereof forming side seams 18 and 19, to define a waist-opening 20 and a pair of leg-openings 21. The front and back portions 2 and 3 are joined along said side seams 18 and 19, for example by adhesive, ultrasonic welding, heat sealing or the like. The front and back portions 2 and 3 may be joined along said side seams with the inner cover 6 facing inwards, as is shown in the drawings. Alternatively they are joined in an overlapped manner with the inner cover 6 of either the front or back portion facing the outer cover 7 of the opposite region.

In an alternative form, the pant diaper comprises a core region comprising the absorbent core, a liquid pervious inner cover and a liquid impervious outer cover as disclosed above, and a chassis region outside the core region, wherein the chassis region comprises a coversheet of a soft and comfortable material, for example an elastic laminate. An example of such a pant diaper is disclosed in PCT/SE2004/001004.

The waist area, at least a part of the leg opening area and the side areas adjacent the side seams 18 and 19 are preferably elasticized. The elastification is usually accomplished by a plurality of elastic members, such as elastic threads 15, contractably affixed in a stretched condition between the outer cover 7 and the inner cover 6. Alternatively elastic materials, such as an elastic laminate, may be used to form the chassis of the article in those areas where elasticity is desired.

FIG. 2 shows the pant diaper in a "flat" state while FIG. 3 shows the same pant diaper in a state where it has been shaped along the folding guides formed by the slits or grooves 17*a, b* to form a narrow crotch width. At the same time the absorbent core 5 forms a "basin"-shape in the crotch region, in which the upraised outer portions of the "basin" are formed by the areas of the absorbent core located between the slits or grooves 17*a-d* and the adjacent longitudinal edge 8 or 9 of the absorbent core 5 and the bottom of the "basin" is formed by the areas of the absorbent core located between the slits or grooves 17*a-d*.

Figure 4:
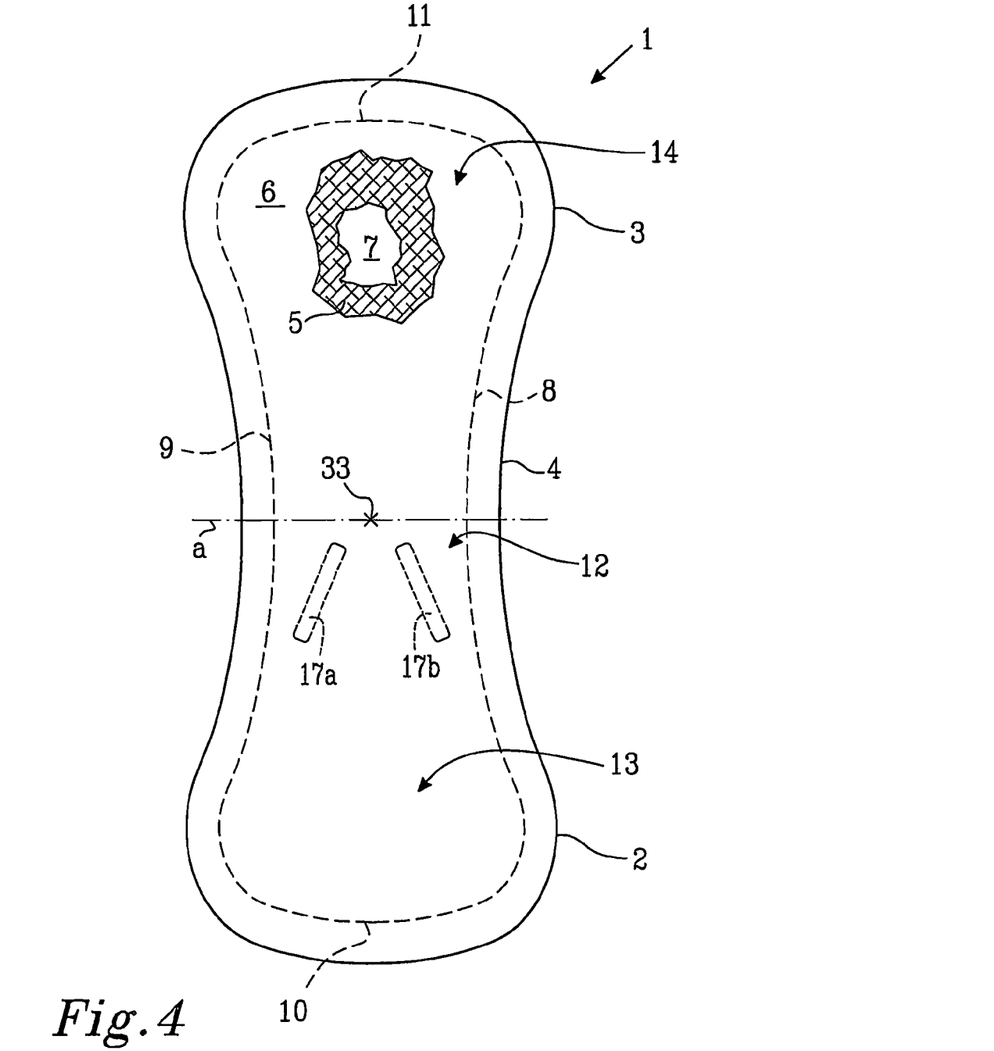
FIG. 4 is a plan view of another embodiment in the form of an incontinence guard or sanitary napkin.

FIG. 4 shows a further embodiment in the form of an incontinence guard or sanitary napkin intended to be worn in the panties of a wearer. Two diverging slits or grooves 17*a* and *b* are arranged in the front part of the crotch region 12 of the absorbent core 5.

Figure 5A:
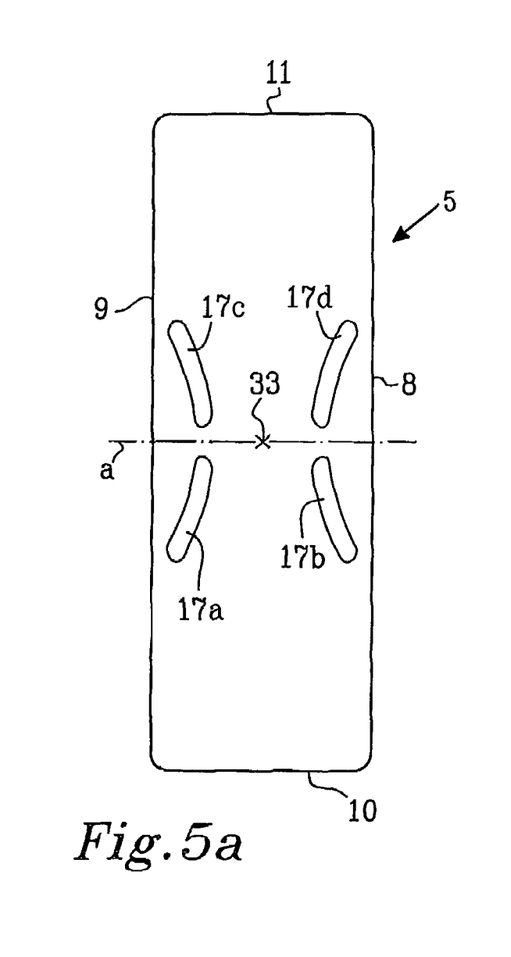
FIG. 5a-c are simplified plan views of some alternative embodiments of an absorbent core according to the invention.
Figure 5B:
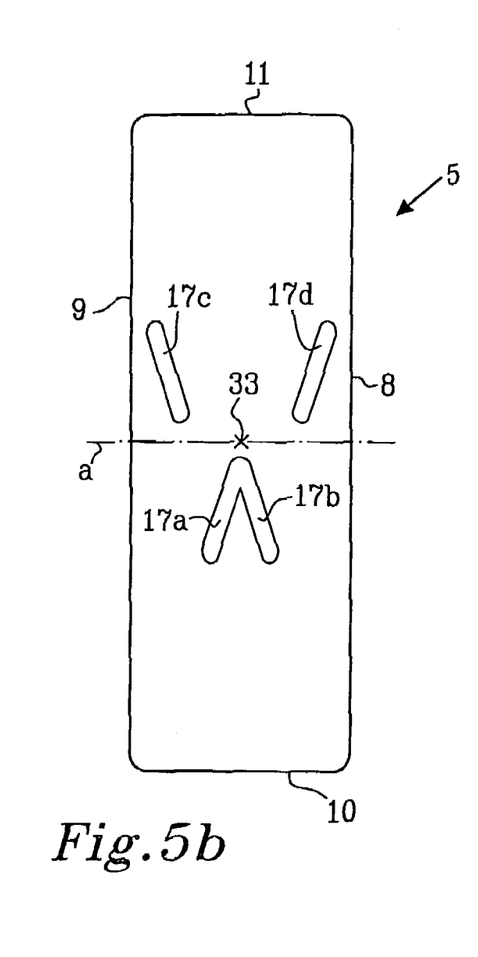
Figure 5C:
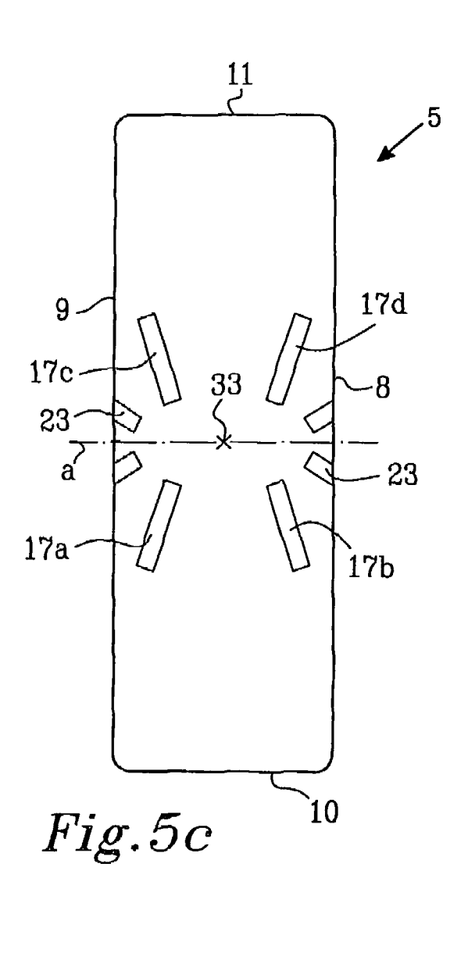

FIG. 5*a-c* show examples of absorbent cores with different configurations of the slits or grooves 17*a-d*.Thus FIG. 5*a* shows that the slits or grooves 17*a-d* have a slightly curved shape. In FIG. 5*b* two slits 17*a, b* are forming a V-shape, so that their converging ends adjacent the crotch area are connected to each other. The other two slits 17*c, d* may of course also be connected to each other at their converging ends to form a V, or be separate from each other, as is shown in FIG. 5*b*.

FIG. 5*c* shows an embodiment in which notches 23 are provided at the respective longitudinal edges of the absorbent core 5 in the crotch area. These notches 23 facilitate the shaping of the absorbent core 5 into the desired "basin" shape. The length of these additional notches 23 are preferably no more than 10 mm.

FIG. 6 illustrates how the crotch point 33 of an absorbent article and of the absorbent core of an absorbent article is determined by placing the article on a wearer in a standing position and then placing an extensible filament 30 around the legs 31, 32 in a figure eight configuration.

It is understood that the number of and configuration of slits or grooves may be varied in the different embodiments and that for example the diaper or pant diaper shown in FIGS. 1-3 may have two slits or grooves as shown in FIG. 4, while the incontinence guard shown in FIG. 4 may for example have four slits or grooves as shown in the other embodiments. The number of slits or grooves is at least two which preferably are arranged in the front region, however may of course alternatively be arranged only in the back portion 3 of the absorbent core 5.

One important advantage of the invention is that even with absorbent cores having a very simple shape in its flat state, such as a rectangular shape, the core can easily be formed into a shape that has a very good fit and a narrow crotch width, while still maintaining a sufficient absorption capacity in the crotch portion and thus a high safety against leakage.

While the present invention has been particularly shown and described with reference to exemplary embodiments thereof, it will be understood by those skilled in the art that various changes in form and details may be made therein without departing from the spirit and scope of the invention as defined by the following claims.

What is claimed is:

1. An absorbent article comprising an absorbent core and a cover enclosing the absorbent core, said absorbent core having either one layer or a plurality of layers, said cover comprising a liquid pervious inner cover on the wearer facing side of the absorbent core and a liquid impervious cover on the garment facing side of the absorbent core, said article having a longitudinal direction extending from a front portion of the article to a rear portion of the article and a transverse direction that is perpendicular to the longitudinal direction, the rear portion either includes fasteners to be fastened to the front portion or is joined to the front portion at a seam, and the article further comprises, as seen in its longitudinal direction, a crotch portion between the front portion and the rear portion, said absorbent core having an elongated shape and comprises a pair of longitudinal edges extending in the longitudinal direction and a front and a back transverse edge, said core having a crotch region and at least one outer region as seen in the longitudinal direction of the article, said outer region or regions being located adjacent the respective transverse edge of the absorbent core, said absorbent core further being provided with at least two slits or grooves, each of said at least two slits or grooves having a first end and a second end and being arranged to extend starting from a location in the crotch region of the absorbent core on one side of a transverse crotch line that extends through a crotch point of the absorbent core, such that both first and second ends are on the one side of the transverse crotch line, to diverge in a direction towards one of the transverse edges that is also on the one side of the transverse crotch line, and to terminate inside the respective longitudinal edge as well as the respective transverse edge of the absorbent core, the crotch point being a point on the absorbent core corresponding to a point of intersection of an extensible filament when wrapped around the legs of a wearer in a figure eight configuration, wherein said at least two slits or grooves extend through the entire thickness of the absorbent core.

2. The absorbent article as claimed in claim 1, wherein said at least two slits or grooves are separated and not directly communicating with each other at their converging ends in the crotch region of the absorbent core.

3. The absorbent article as claimed in claim 1, wherein said at least two slits or grooves are communicating with each other at their converging ends in the crotch region of the absorbent core so as to form a V-shape.

4. The absorbent article as claimed in claim 1, wherein said at least two slits or grooves are areas having a lower basis weight than the surrounding areas of the absorbent core.

5. The absorbent article as claimed in claim 1, wherein said at least two slits or grooves are cuts.

6. The absorbent article as claimed in claim 1, wherein said at least two diverging slits or grooves form an angle of between 5° and 135° to each other.

7. The absorbent article as claimed in claim 1, wherein said at least two diverging slits or grooves form an angle of from 10° to 120° to each other.

8. The absorbent article as claimed in claim 1, wherein said slits or grooves have a length of at least 20 mm.

9. The absorbent article as claimed in claim 1, wherein said slits or grooves have a width of from 1 to 25 mm.

10. The absorbent article as claimed in claim 1, wherein said at least two slits or grooves are arranged to diverge in a direction towards the front transverse edge of the absorbent core.

11. An absorbent article as claimed in claim 10, wherein at least four slits or grooves are provided, at least two of which are diverging in a direction towards the front transverse edge and at least two are diverging in a direction towards the back transverse edge of the absorbent core.

12. The absorbent article as claimed in claim 11, wherein the at least two slits or grooves diverging towards the front transverse edge are spaced apart from the at least two slits or grooves diverging towards the back transverse end a smallest distance in the longitudinal direction of at least 20 mm.

13. The absorbent article as claimed in claim 11, wherein at least two slits or grooves diverging towards the front transverse edge and the at least two slits or grooves diverging towards the back transverse end are arranged on opposite sides of a transverse crotch line extending through a crotch point.

14. The absorbent article as claimed in claim 11, wherein the at least two slits or grooves diverging towards the front transverse edge are spaced apart from the at least two slits or grooves diverging towards the back transverse end a smallest distance in the longitudinal direction of at least 5 mm.

15. The absorbent article as claimed in claim 1, wherein one or more notches are provided at the respective longitudinal edges of the absorbent core in the crotch region thereof.

16. The absorbent article as claimed in claim 1, wherein the absorbent core has a substantially rectangular shape.

17. The absorbent article as claimed in claim 1, wherein said at least two diverging slits or grooves form an angle of from 20° to 60° to each other.

18. The absorbent article as claimed in claim 1, wherein said slits or grooves have a length of at least 30 mm.

19. The absorbent article as claimed in claim 1, wherein said slits or grooves have a width of from 5 to 15 mm.

20. The absorbent article as claimed in claim 1, wherein the rear portion includes fasteners to be fastened to the front portion.

21. The absorbent article as claimed in claim 1, wherein the rear portion is joined to a front portion at a seam.

22. An absorbent article comprising an absorbent core and a cover enclosing the absorbent core, said absorbent core having either one layer or a plurality of layers, said cover comprising a liquid pervious inner cover on the wearer facing side of the absorbent core and a liquid impervious cover on the garment facing side of the absorbent core, said article having a longitudinal direction extending from a front portion of the article to a rear portion of the article and a transverse direction that is perpendicular to the longitudinal direction, and the article further comprises, as seen in its longitudinal direction, a crotch portion between the front portion and the rear portion, said absorbent core having a longitudinal axis and elongated shape, and comprises a pair of longitudinal edges extending in the longitudinal direction and a front and a back transverse edge, said core having a crotch region and at least one outer region as seen in the longitudinal direction of the article, said outer region or regions being located adjacent the respective transverse edge of the absorbent core, said absorbent core further being provided with at least two slits or grooves, said at least two slits or grooves are arranged to extend from the crotch region of the absorbent core toward a respective one of the transverse edges and said at least two slits or grooves diverge outwardly from the longitudinal axis as said at least two slits or grooves extend in a direction that extends from a transverse crotch line extending through a crotch point of the absorbent core towards the respective one of the transverse edges of the absorbent core over the entire length of each respective slit or groove, and to terminate inside the respective longitudinal edge as well as the respective transverse edge of the absorbent core, said at least two slits or grooves being longitudinally offset from the transverse centerline, and the crotch point being a point on the absorbent core corresponding to a point of intersection of an extensible filament when wrapped around the legs of a wearer in a figure eight configuration, wherein said at least two slits or grooves extend through the entire thickness of the absorbent core.

23. The absorbent article as claimed in claim 20, wherein the crotch point is located at a longitudinal center of the crotch region.

24. An absorbent article comprising an absorbent core and a cover enclosing the absorbent core, said absorbent core having either one layer or a plurality of layers, said cover comprising a liquid pervious inner cover on the wearer facing side of the absorbent core and a liquid impervious cover on the garment facing side of the absorbent core, said article having a longitudinal direction extending from a front portion of the article to a rear portion of the article and a transverse direction that is perpendicular to the longitudinal direction, the rear portion either includes fasteners to be fastened to the front portion or is joined to the front portion at a seam, and the article further comprises, as seen in its longitudinal direction, a crotch portion between the front portion and the rear portion, said absorbent core having a longitudinal axis and elongated shape, and comprises a pair of longitudinal edges extending in the longitudinal direction and a front and a back transverse edge, said core having a crotch region and at least one outer region as seen in the longitudinal direction of the article, said outer region or regions being located adjacent the respective transverse edge of the absorbent core, said absorbent core further being provided with at least two slits or grooves, said at least two slits or grooves are arranged to extend from the crotch region of the absorbent core toward a respective one of the transverse edges and said at least two slits or grooves diverge outwardly from the longitudinal axis as said at least two slits or grooves extend in a direction that extends from a transverse crotch line extending through a crotch point of the absorbent core towards the respective one of the transverse edges of the absorbent core over the entire length of each respective slit or groove, and to terminate inside the respective longitudinal edge as well as the respective transverse edge of the absorbent core, said at least two slits or grooves being longitudinally offset from the transverse centerline, and the crotch point being a point on the absorbent core corresponding to a point of intersection of an extensible filament when wrapped around the legs of a wearer in a figure eight configuration, wherein said at least two slits or grooves extend through the entire thickness of the absorbent core.

* * * * *